United States Patent [19]

Rasnick et al.

[11] Patent Number: 4,505,852

[45] Date of Patent: Mar. 19, 1985

[54] 7-AMINO-4-TRIFLUOROMETHYLQUINO-LONE DERIVED SUBSTRATES AND METHOD FOR DETERMINING ENZYMES AND INHIBITORS

[75] Inventors: David W. Rasnick, Sunol; Eugene R. Bissell, Alamo, both of Calif.

[73] Assignee: Enzyme Systems Products, Dublin, Calif.

[21] Appl. No.: 445,280

[22] Filed: Nov. 29, 1982

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 4,379,764 4/1983 Fujii et al. ..................... 260/112.5 R
4,406,832 9/1983 Mills ............................. 260/112.5 R
4,409,140 10/1983 Smith et al. .................. 260/112.5 R

OTHER PUBLICATIONS

Chem. Abstr., vol. 84, (1976), 128535e.
J. Org. Chem., 1980, 45, 2283–2287.

Primary Examiner—Delbert R. Phillips
Attorney, Agent, or Firm—Paul Davis

[57] ABSTRACT

Substrates and their corresponding pharmaceutically acceptable acid salts derived from 7-amino-4-trifluoromethyl-quinolone are disclosed. These substrates are useful for determining the presence of an enzyme or enzyme inhibitor in a biological fluid, wherein the fluid is contacted with a substrate. This mixture is thereafter incubated to effect enzymatic hydrolysis. Subsequently, the presence of the free 7-amino-4-trifluoro-methyl-quinolone is fluorometrically detected.

20 Claims, No Drawings

7-AMINO-4-TRIFLUOROMETHYLQUINOLONE DERIVED SUBSTRATES AND METHOD FOR DETERMINING ENZYMES AND INHIBITORS

BACKGROUND

This invention relates to synthetic substrates and their uses in determining the presence of enzymes, and more particularly, to derivatives of 7-amino-4-trifluoromethyl-quinolone and process employing such derivatives to determine the presence of proteolytic enzymes.

The determination of specific enzymes and biological fluids including but not limited to blood, tissue homogenates, and protoplasm is very useful for the diagnosis of certain diseases.

Synthetic substrates have been developed and utilized for such determinations, resulting in clinical assay procedures having a high degree of specificity, reliability and sensitivity. Synthetic substrates have generally been amino acid derivatives of aromatic amines.

The number and arrangement of amino acids in the peptide moiety determines the enzyme specificity of a substrate. Any enzyme activity is measured by the amount of aromatic amine moiety liberated upon hydrolysis of a substrate. Generally, the process wherein an enzyme cleaves a substrate to liberate either a fluorophor or a chromophor is illustrated by the following:

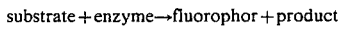

Exemplary synthetic substrates are disclosed in U.S. Pat. No. 3,862,011, dated Jan. 21, 1975, to Smith, and in U.S. Pat. No. 4,294,923, dated Oct. 13, 1981, to Smith et al.

Inherent in the reliability and sensitivity of clinical assay procedures employing synthetic substrates is the shift in the emission wavelengths between the synthetic substrate and the liberated fluorophor. Upon enzyme hydrolysis of the fluorogenic synthetic substrate, a shifting toward the red end of the emission wavelengths between the synthetic substrate and the liberated fluorophor occurs. The greater the shift, the greater the reliability of detecting the liberated fluorophor.

It would be an advancement in the art and highly desirable to develop a synthetic substrate which has a long wavelength shift, as well as possessing properties which would make it useful for the determination of specific enzymes and inhibitors in biological fluids.

SUMMARY OF THE INVENTION

Accordingly, it is an object of the present invention to provide synthetic substrates which are useful for determining the presence of an enzyme or an enzyme inhibitor in an enzyme-containing anylate.

Another object of the present invention is to provide synthetic substrates which are useful for determining the presence of an enzyme or an enzyme inhibitor in an enzyme-containing anylate wherein the fluorescent shift observed between the synthetic substrate and the liberated fluorophor is relatively large.

Additional objects, advantages, and novel features of the invention will be set forth in part in the description which follows, and in part will become apparent to those skilled in the art upon examination of the following, or may be learned by practice of the invention. The objects and advantages of the invention may be realized and obtained by means of the instrumentalities and combinations particularly pointed out in the appended claims.

To achieve the foregoing and other objects, and in accordance with the purposes of the present invention, as embodied and broadly described herein, the synthetic substrates (and their corresponding salts) of the present invention have the following formula:

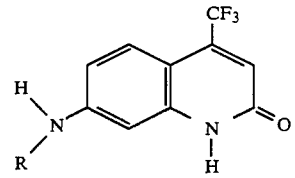

wherein R is an amino acid, a peptide, or a derivative thereof.

In a further aspect of the present invention, in accordance with its objects and purposes, the method for determining presence of an enzyme or an enzyme inhibitor in an enzyme-containing anylate comprises contacting the anylate with a substrate having the above recited formula. The analyte-substrate mixture is incubated under enzyme hydrolyzing conditions as to form an enzyme hydrolyzate. Upon enzyme hydrolysis, the fluorophor 7-amino-4-trifluoromethylquinolone (AFQ) is fluorometrically detected in the enzyme hydrolyzate.

Synthetic substrates of the present invention provide upon enzyme hydrolysis an unexpectedly superior fluorescent shift. Additionally, the liberated 7-amino-4-trifluoromethylquinolone fluoresces strongly in the green region of the spectrum which minimizes background interference. Such fluorescence is advantageous because it can be measured with relatively inexpensive instruments. The synthetic substrates of the present invention are particularly useful in the following assays: measurement of plasminogen in plasma; evaluation of antithrombin III in plasma; measurement of heparin in plasma; measurement of antiplasmin in plasma; measurement of glandular kallikrein in blood; and measurement of plasma kallikrein in blood.

DETAILED DESCRIPTION OF THE INVENTION

The substrates (and their corresponding pharmaceutically acceptable salts, specifically hydrochloride, dihydrochloride, hydrobromide, dihydrobromide, trifluoroacetic and ditrifluoroacetic) of the present invention are represented by the formula

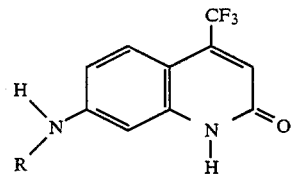

wherein R is a single amino acid or peptide, consisting of two or more amino acids. The terminal amino acid may be reacted with any suitable blocking groups as is well known in the art including but not limited to carbobenzoxy, benzoyl, glutaryl, t-butoxycarbonyl, and certain d-amino acids, e.g., d-proline, d-valine, or d-alanine.

Upon ezymatic hydrolysis, the fluorophor 7-amino-4-trifluoromethyl-quinolone (hereinafter AFQ) is released. This fluorophor fluoresces strongly in the green region of the spectrum at 500 nm when irradiated with ultraviolet light, however, the intact substrates fluoresce very weakly, if at all, in that region. The fluorescent shift between the liberated fluorophor and the substrate is 70 to 80 nm. These properties make the substrates particularly useful for enzyme assays.

The number and arrangement of amino acids attached to the fluorophor determine the enzyme specifity for the substrate. Any combination of amino acids can be employed to obtain the desired specifity. Preferably, the amino acid chain consists of about 1 to 12 amino acids. Most preferably, the chain consists of from about 1 to 4 amino acids. The amino acids are bound together through peptide bonds.

The amino acid chain can be terminated with a blocking group. Such a blocking group may be employed during a synthesis of the substrate to prevent reactions with the terminal amino acid, and a blocking group is sometimes employed in substrates to improve the enzyme specifity. Suitable blocking groups include but are not limited to carbobenzoxy, benzoyl, glutaryl, t-butoxycarbonyl, and certain d-amino acids including but not limited to d-proline, d-valine, and d-alanine.

Preferred substrates (and their corresponding acid salts) of the present invention are compounds represented by the above formula wherein R is carbobenzoxy-Arginyl; Arginyl; carbobenzoxy-Prolyl-Arginyl; Boc-d-Phenylalanyl-Prolyl-Arginyl; d-Phenylalanyl-Prolyl-Arginyl; α-carbobenzoxy-ε-Boc-lysyl; ε-Boc-Lysyl; Boc-d-Valyl-Leucyl-ε-Boc-Lysyl; d-Valyl-Leucyl-Lysyl; Leucyl-Arginyl; Boc-d-Valyl-Leucyl-Arginyl; d-Valyl-Leucyl-Arginyl; Lysyl(ε-carbobenzoxy)-Arginyl; Lysyl(ε-carbobenzoxy)-Lysyl(ε-carbobenzoxy)-Arginyl; and d-Valyl-Lysyl(ε-carbobenzoxy)-Lysyl(ε-carbobenzyoxy)-Arginyl.

These substrates are prepared by incubating AFQ with an appropriate amino acid or pepide. Such incubation is accomplished by $PCl_3$ condensation. Additionally, amino acids or peptides can be added to substrates having one or more unblocked amino acids. Any desired number and arrangement of amino acids can be added onto the fluorophor. Blocking groups can be removed, e.g., by hydrogenolysis or treatment with an anhydrous hydrogen bromide in acetic acid, trifluoroacetic acid or other conventional deblocking agents as are well known in the art.

The method of the present invention for determining the presence of an enzyme or an enzyme inhibitor in an enzyme-containing analyte comprises contacting the analyte with a substrate which can be hydrolyzed with an enzyme. Such analyte is usually a natural biological fluid including but not limited to blood, serum, urine, tissue homogenate, and the like, but can also be a synthetic solution used for quality control or as a reference standard. Generally, the substrate is employed in excess of the amount which can be completely hydrolyzed by the quantity of enzyme or inhibitor present.

The analyte substrate mixture is incubated under enzyme hydrolyzing conditions to form an enzyme hydrolyzate. Such enzyme hydrolyzing conditions include conditions of pH and temperature which are conducive to the enzymatic hydrolysis of the substrate. The pH of the analyte substrate mixture is generally in the range of the normal physiological environment of the enzyme or inhibitor, and thus can vary from one enzyme or inhibitor to another. The pH of the mixture is conveniently controlled by dissolving the analyte and substrate in an appropriate buffer including but not limited to N-tris(hydroxymethyl) (methyl-2-aminoethane sulfonic acid)(TES), and the like.

The temperature at which the enzyme hydrolysis is effected is not critical, and may fall within a broad range, provided that the temperature is high enough to ensure enzyme activity, but not too high to cause degradation or other harmful reactions involving the substrate, the enzyme, or other components of the mixture.

The fluorometric determination of the liberated fluorophor can be either a rate determination or an end point determination. Rate determinations are preferred, because they are generally more sensitive and precise. In a rate determination, the fluorescence of the substrate analyte mixture may be determined promptly after the analyte is contacted with the substrate. In an end point determination, the enzyme hydrolysis reaction is allowed to proceed for a predetermined length of time, e.g., for about 5 to about 60 minutes, preferably from about 15 to about 30 minutes. Such reaction time is selected so that a sufficient quantity of fluorophor has been released as to provide an acceptable degree of accuracy for the assay.

For fluorometric assays, excitation and emission wavelengths can be selected to conform to existing equipment available in clinical laboratories. Maximum excitation and emission wavelengths for the AFQ fluorophor are 385 nm and 500 nm, respectively. The absorbance maximum wavelength for the liberated AFQ fluorophor is about 385 nm.

Substrates of this invention are useful for a variety of analytical techniques. They can be utilized in biological studies to indicate the presence of certain enzymes in single cells. Other uses of the substrates include their utilization as indicators for various chromatographic or electrophoretic techniques. Enzymes can be isolated by chromatography, e.g., paper chromatography, thin layer chromatography, or column chromatography, or by electrophoresis. The appropriate substrate can be applied to the chromatographic or electrophoretic medium to indicate the location or density of the enzyme spot, band, or zone.

The following examples are illustrative of the present invention and are not to be regarded as limiting in scope which is defined in the appended claims:

EXAMPLE 1

Synthesis of 7-Amino-4-Trifluoromethylquinolone (AFQ)

m-Phenylenediamine (28.84 g, 0.26 mole), ethyl trifluoroacetoacetate (49.12 g, 0.26 mole), and $ZnCl_2$ (44 g) were refluxed in 280 ml ethanol containing 10 ml isopropanol for 18 hours. The reaction mixture was poured into 1600 ml iced water containing 10 ml. conc. HCl and let stand at room temperature 2 hours. The solid was filtered, washed with water and air dried. The product was recrystallized from 800 ml boiling ethanol to give 18.63 g (31%) 7-amino-4-trifluoromethylquinolone (AFQ).

EXAMPLE 2

Synthesis of Carbobenzoxy-Arginyl-AFQ-HCl

To AFQ (10 g, 43.82 m mol) suspended in 250 ml pyridine cooled to 0° C. was added $PCl_3$ (2.56 ml, 29.36 m mol) and stirred 0.5 hour at room temperature. Carbobenzoxy-arginine (13.49 g, 43.82 m mol) was added to the reaction and refluxed 4 hours. The solvent was removed by evaporation. The residue was taken up in chloroform/methanol (10:1) and poured into a 10 fold excess of ether. The solvent was decanted and the residue overlayed with 1N HCl at 4° C. for 20 hours. The solid material was collected and taken up in chloroform and poured into 10 fold excess of ether. The solid was filtered and pumped dry to give 7.06 g (29%) carbobenzoxy-Arginyl-AFQ·HCl.

EXAMPLE 3

Synthesis of Arginyl-AFQ Dihydrobromide

Carbobenzoxy-Arginyl-AFQ (5 g, 9.03 m mol) was treated with 20 ml 30% HBr-acetic acid for 0.5 hour. The reaction was diluted with an equal volume of chloroform and poured into 500 ml ether. The solid was filtered, washed several times with ether and pumped dry over KOH to give 4.67 g (95%) arginyl-AFQ dihydrobromide.

EXAMPLE 4

Synthesis of Carbobenzoxy-Prolyl-Arginyl-AFQ Hydrobromide

To carbobenzoxy-Prolyl-OTCP (4 g, 9.24 m mol) and Arginyl-AFQ dihydrobromide (4.60 g, 8.40 m mol) in DMF (20 ml) were added 4-methyl-morpholine (2.3 ml) and HOBT (100 mg). The reaction was stirred at room temperature for 20 hours. The solvent was removed by evaporation and the residue was taken up in chloroform (100 ml) and poured into one liter ether. The solid was filtered, washed with ether and pumped dry to give 3.10 g (97%) carbobenzoxy-Prolyl-Arginyl-AFQ hydrobromide.

EXAMPLE 5

Synthesis of Boc-d-Phenylalanyl-Prolyl-Arginyl-AFQ Hydrobromide

Carbobenzoxy-Prolyl-Arginyl-AFQ hydrobromide (6.80 g, 9.77 m mol) was taken up in 200 ml DMF and treated with 2 g 5% Pd on carbon. Nitrogen was bubbled in for 5 min followed by hydrogen for 2.5 hours, at which time the reaction was complete. Nitrogen was then bubbled in for 5 min. The catalyst was removed and Boc-d-Phenylalanyl-OCTP (4.77 g, 10.7 m mol) was added to the DMF solution along with 4-methyl-morpholine (1.18 ml) and HOBT (100 mg). The reaction was stirred 20 hours at room temperature. The DMF was evaporated off under reduced pressure and the residue taken up in chloroform (150 ml) and poured into one liter ether. The solid was filtered, washed with ether, and pumped dry to give 5.56 g (70%) Boc-d-Phenylalanyl-Propyl-Arginyl-AFQ hydrobromide.

EXAMPLE 6

Synthesis of d-Phenylalanyl-Prolyl-Arginyl-AFQ Ditrifluoroacetate

Boc-d-Phenylalanyl-Prolyl-Arginyl-AFQ hydrobromide (5.56 g, 6.87 m mol) was treated with trifluoroacetic acid 1 hour at room temperature. The solution was diluted with an equal volume of dichloromethane and poured into ether (500 ml). The solid was filtered, washed with ether, and pumped dry to give 4.88 g (83%) d-Phenylalanyl-Prolyl-Arginyl-AFQ ditrifluoroacetate. Traces of free AFQ were removed by treating a chloroform/methanol solution of the product with Norit A, followed by filtration and precipitation with ether.

EXAMPLE 7

Synthesis of α-Carbobenzoxy-ε-Boc-Lysyl-AFQ

To α-carbobenzoxy-ε-Boc Lysine (20.0 g, 52.6 m mol) in THF (250 ml) containing pyridine (4.25 ml, 52.6 m mol) at −10° C. was added thionyl chloride (3.8 ml, 52.6 m mol). The temperature rose to 0° C. The mixture was stirred 0.5 hour at −10° C. then a precooled solution of AFQ (12.0 g, 52.6 m mol) in 300 ml THF containing pyridine (4.25 ml, 52.6 m mol) was added. The ice bath was removed and the reaction stirred 20 hours at room temperature. The mixture was filtered and the filtrate evaporated at reduced pressure. The residue was taken up in ethyl acetate and washed with 10% citric acid, saturated NaHCO₃, and brine. The organic layer was dried over MgSO₄ and the ethyl acetate removed by evaporation. The residue was taken up in 200 ml ether and poured into one liter petroleum ether. The solid was filtered, washed with petroleum ether and pumped dry to give 15.8 g (51%) α-carbobenzoxy-ε-Boc-Lysine-AFQ.

EXAMPLE 8

Synthesis of ε-Boc-Lysyl-AFQ

α-carbobenzoxy-ε-Boc-Lysyl-AFQ (12.5 g, 21.2 m mol) was taken up in ethanol (500 ml) and treated with 3.1 g 5% Pd on carbon. Nitrogen was bubbled in 5 minutes followed by hydrogen for 3 hours at 55° C. Nitrogen was bubbled in 5 minutes and the catalyst removed. The ethanol was removed by evaporation and the residue pumped to a foam to give 8.51 g (88%) ε-Boc-Lysyl-AFQ.

EXAMPLE 9

Synthesis of Boc-d-Valyl-Leucyl-ε-Boc-Lysyl-AFQ

To Boc-d-Valyl-Leucine (6.16 g, 18.7 m mol) and ε-Boc-d-Lysyl-AFQ (8.51 g, 18.7 m mol) in 300 ml dichloromethane containing HOBT (2.52 g, 18.7 m mol) at 0° C. was added DDC (4.23 g, 20.5 m mol). The reaction was stirred 1 hour at 0° C. then allowed to warm to room temperature over 20 hours. The mixture was filtered and the solvent removed by evaporation. The residue was taken up in ethyl acetate and washed with 10% citric acid, saturated NaHCO₃, and brine. The organic layer was dried over MgSO₄ and the solvent removed by evaporation. The residue was pumped to a foam to give 11.18 g (78%) Boc-d-Valyl-Leucyl-ε-Boc-Lysyl-AFQ.

EXAMPLE 10

Synthesis of d-Valyl-Leucyl-Lysyl-AFQ Ditrifluoroacetate

Boc-d-Valyl-Leucyl-ε-Boc-Lysyl-AFQ (6.2 g, 8.07 m mol) was suspended in 50 dichloromethane and treated with trifluoroacetic acid (25 ml) for 1 hour at room temperature. The solution was then poured into 700 ml ether. The solid was filtered, washed with ether, and pumped dry to give 5.92 g (92%) d-Valyl-Leucyl-Lysyl-AFQ ditrifluoroacetate.

EXAMPLE 11

Synthesis of Leucyl-Arginyl-AFQ Dihydrochloride

To Arginyl-AFQ 2HBr (1.8 g, 3.30 m mol) in 20 ml DMF were added Boc-Leucyl-OTCP (1.5 g, 3.63 m mol), N-methylmorpholine (0.90 ml, 8.24 m mol), and hydroxybenzotriazole (50 mg). The solution was stirred 20 hours at room temperature. The solvent was removed by evaporation and the residue taken up in chloroform-methanol (9:1) (30 ml) and poured into 500 ml ether. The solid was filtered, washed with ether and pumped dry to give a white solid. The material was taken up in dichloromethane containing an equal volume HCl-dioxane. The solution was protected with a CaCl₂ drying tube. After 45 minutes the whole was diluted with 500 ml ether. The solid was filtered, washed with ether and pumped dry to give 1.33 g (71%) Leucyl-Arginyl-AFQ dihydrochloride.

EXAMPLE 12

Synthesis of Boc-d-Valyl-Leucyl-Arginyl-AFQ Hydrochloride

To Leucyl-Arginyl-AFQ 2HCl (1.33 g, 2.33 m mol) in 10 ml DMF were added Boc-d-Valyl-OTCP (1.2 g, 3.03 m mol), N-methylmorpholine (0.64 ml, 5.83 m mol), and hydroxybenzotriazole (50 mg). The reaction was stirred at room temperature 20 hours. The solvent was removed by evaporation. The residue was taken up in chloroform-methanol (9:1) and poured into 400 ml ether. The solid was filtered, washed with ether and pumped dry to give 1.1 g (65%) Boc-d-Valyl-Leucyl-Arginyl-AFQ hydrochloride.

EXAMPLE 13

Synthesis of d-Valyl-Leucyl-Arginyl-AFQ Ditrifluoroacetate

To Boc-d-Valyl-Leucyl-Arginyl-AFQ HCl (1.1 g, 1.50 m mol) suspended in 15 ml dichloromethane was added trifluoroacetic acid (10 ml). The solution was stirred 1 hour at room temperature then poured into ether (300 ml). The solid was filtered, washed with ether and pumped dry over sodium hydroxide pellets to give 0.94 g (76%) d-Valyl-Leucyl-Arginyl-AFQ ditrifluoroacetate.

EXAMPLE 14

Synthesis of Lysyl(ε-Carbobenzoxy)-Arginyl-AFQ Dihydrochloride

To Arginyl-AFQ 2HBr (1.85 g, 3.39 m mol) in 20 ml DMF were added α-Boc-ε-carbobenzoxy-Lysyl-OSu (1.78 g, 3.73 m mol) and triethylamine (0.52 ml, 3.73 m mol). The solution was stirred at room temperature 20 hours. The solvent was removed by evaporation. The residue was taken up in chloroform (20 ml) and poured into 300 ml ether. The solid was filtered, washed with ether, and pumped dry to give a white solid. The material was dissolved in 20 ml dichloromethane and treated with 20 ml HCl-dioxane for 30 minutes at 0° C. The reaction was diluted with ether (300 ml). The solid was filtered, washed with ether, and pumped dry over sodium hydroxide pellets to give 2.07 g (85%) Lysyl(ε-carbobenzoxy)-Arginyl-AFQ dihydrochloride.

EXAMPLE 15

Synthesis of Lysyl(ε-Carbobenzoxy)-Lysyl(ε-Carbobenzoxy)-Arginyl-AFQ Dihydrochloride To Lysyl(ε-carbobenzoxy)-Arginyl-AFQ 2HCl (2.06 g, 2.87 m mol) in 20 ml DMF were added α-Boc-ε-carbobenzoxy-Lysyl-OSu (1.5 g, 3.15 m mol) and triethylamine (0.40 ml, 2.87 m mol). The solution was stirred 20 hours at room temperature. The reaction was filtered and the filtrate evaporated to dryness. The residue was taken up in chloroform (50 ml) and poured into ether (600 ml). The solid was filtered, washed with ether, and pumped dry to give a white solid. The material was taken up in 20 ml dichloromethane and treated with 20 ml HCl-dioxane for 30 minutes at 0° C. The reaction was diluted with ether (400 ml). The solid was filtered, washed with ether, and pumped dry over sodium hydroxide pellets to give 2.33 g (83%) Lysyl(ε-carbobenzoxy)-Lysyl(ε-carbobenzoxy)-Arginyl-AFQ dihydrochloride.

EXAMPLE 16

Synthesis of d-Valyl-Lysyl(ε-Carbobenzoxy)-Lysyl-(ε-Carbobenzoxy)-Arginyl-AFQ Ditrifluoroacetate To Lysyl(ε-carbobenzoxy)-Lysyl(ε-carbobenzoxy)-Arginyl-AFQ 2HCl (2.33 g, 2.38 m mol) in 25 ml DMF were added Boc-d-Valyl-OTCP (1.04 g, 2.62 m mol), N-methylmorpholine (0.65 ml, 5.95 m mol), and hydroxybenzotriazole (50 mg). The solution was stirred at room temperature 20 hours. The solvent was removed by evaporation and the residue taken up in chloroform (50 ml) and poured into ether (400 ml). The solid was filtered, washed with ether, and pumped dry to give a white solid. The material was taken up in 20 ml dichloromethane and treated with 20 ml trifluoroacetic acid for 30 minutes. The reaction was diluted with ether (300 ml). The solid was filtered, washed with ether, and pumped dry over sodium hydroxide pellets to give 0.92 g (31%) d-Valyl-Lysyl(ε-carbobenzoxy)-Lysyl(ε-carbobenzoxy)-Arginyl-AFQ ditrifluoroacetate.

EXAMPLE 17

Measurement of Plasminogen in Plasma

The enzyme streptokinase combines with plasminogen and the resulting activity is measured with the synthetic plasmin substrate D-val-leu-lys-AFQ. The non-fluorescent substrate is cleaved to yield the fluorescent compound AFQ which is measured at excitation 385 nm/emission 500 nm. The reaction is illustrated by the following equation:

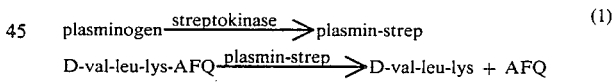

$$\text{plasminogen} \xrightarrow{\text{streptokinase}} \text{plasmin-strep} \quad (1)$$

$$\text{D-val-leu-lys-AFQ} \xrightarrow{\text{plasmin-strep}} \text{D-val-leu-lys} + \text{AFQ}$$

Fluorescence Reference Solution

A 15 μg/ml solution of AFQ in tris buffer pH 8.2 is used as the fluorescence reference. This solution is prepared from a concentrated stock solution of AFQ in dimethyl formamide (10 mg/ml).

Substrate Reagent

A 10 mg/ml solution of D-val-leu-lys-AFQ in dimethyl formamide serves as a stock. Working substrate solution is a 100 μg/ml solution of substrate in the tris buffer pH 8.2.

Streptokinase Reagent

A 2,000 units/ml solution of streptokinase in the buffer tris pH 8.2 is used as a second reagent.

A sample of plasma is allowed to react with the substrate and the fluorescence measurement at excitation 385 nm/emission 500 nm to indicate the level of plasminogen in plasma.

EXAMPLE 18

Evaluation of Antithrombin III in Plasma

Plasma antithrombin III is quantitated indirectly through the inhibition of thrombin by AT III·heparin complex. Plasma is incubated with a thrombin-heparin mixture and the residual thrombin activity is measured with the aid of the synthetic substrate D-phe-pro-arg-AFQ.

The synthetic substrate (peptide-AFQ) is cleaved by thrombin releasing the fluorescent compound AFQ which is measured at excitation 385 nm/emission 500 nm as illustrated by the following equation:

AT III+heparin+thrombin→AT III·thrombin·heparin+residual thrombin residual thrombin+peptide·AFQ→peptide+AFQ    (2)

Buffer

A 0.1M tris buffer pH 8.2 solution is used.

Fluorescence Reference Solution

A 15 μg/ml solution of AFQ in tris buffer pH 8.2 is used as the fluorescence reference. This solution is prepared from a concentrated stock solution of AFQ (i.e., 10 mg/ml) in dimethyl formamide.

Substrate Reagent

A stock solution of 10 mg D-phe-pro-arg-AFQ/ml is made using dimethyl formamide as solvent. Working substrate solution is 100 μg/ml solution of the substrate in the tris buffer pH 8.2.

A sample of plasma is allowed to react with the substrate reagent and the fluorescence measured at excitation 385 nm/emission 500 nm to quantitate plasma antithrombin III in plasma.

EXAMPLE 19

Measurement of Heparin in Plasma

The synthetic substrate D-phe-pro-arg-AFQ (peptide-AFQ) is cleaved by thrombin, releasing the fluorescent molecule AFQ. Heparin in the presence of its cofactor antithrombin III is an inhibitor of thrombin and is indirectly measured as the percent thrombin activity remaining as illustrated by the following equation:

Antithrombin III+Heparin→AT III·Heparin AT III·Heparin+Thrombin→AT III·Heparin·Thrombin+Residual Thrombin    (3)

Residual Thrombin+D-phe-pro-arg-AFQ→D-phe-pro-arg+AFQ

Buffer

A 0.1M tris buffer pH 8.2 solution is used.

Fluorescence Reference Solution

A 15 μg/ml solution of AFQ in tris buffer pH 8.2 is used. This solution is prepared from a concentrated stock solution of AFQ (i.e., 10 mg/ml) in dimethyl formamide.

Substrate Reagent

A stock solution of 10 mg D-phe-pro-arg-AFQ/ml is made using dimethyl formamide as solvent. Working substrate solution is a 100 μg/ml solution of peptide AFQ in the tris buffer pH 8.2.

A sample of plasma is allowed to react with the substrate reagent and the fluorescence measured at excitation 385 nm/emission 500 nm to measure the amount of heparin in the plasma sample.

EXAMPLE 20

Measurement of Antiplasmin in Plasma

Antiplasmin in plasma is measured using the substrate D-val-leu-lys-AFQ and the reagents disclosed in Example 18. Fluorescence is again measured at excitation 385 nm/emission 500 nm.

EXAMPLE 21

Measurement of Glandular Kallikrein

Glandular kallikrein in blood is assayed by using a 0.02 mm solution of the substrate D-val-leu-arg-AFQ in 0.1M TES buffer containing 100 μg/ml of soybean trypsin inhibitor. Free AFQ is liberated and the fluorescence measured at excitation 385 nm/emission 500 nm. 5 μl of blood sample/200 μl total volume of solution is employed.

EXAMPLE 22

Measurement of Plasma Kallikrein

The amount of plasma kallikrein in blood is assayed with the substrate D-val-lys(ε-carbobenzoxy)-lys(ε-carbobenzoxy)-Arginyl-AFQ. 50 μl of plasma is pre-incubated for 15 minutes with 50 μl of solution comprising 70% acetone and 30% H₂O with dexitrane sulfate 500,000 MW (1 μg/ml). The sample is then diluted with 3000 μl of 0.1 TES buffer pH 8.2, allowed to react with the substrate and the fluorescence of the liberated AFQ measured at excitation 385 nm/emission 500 nm.

The foregoing description of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A synthetic substrate of the formula and its corresponding pharmaceutically acceptable salts

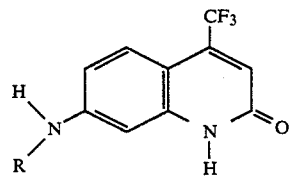

wherein R is a single amino acid or a peptide chain.

2. The synthetic substrate of claim 1, wherein R is a peptide chain of about 1 to 12 amino acids.

3. The synthetic substrate of claim 1, wherein R is a peptide chain of about 1 to 4 amino acids.

4. The synthetic substrate of claim 1, wherein R terminates with an end-blocking group selected from carbobenzoxy, benzoyl, glutaryl, t-butyloxycarbonyl, d-proline, d-valine, and d-alanine.

5. The synthetic substrate of claim 1, wherein R is selected from carbobenzoxy-Arginyl; Arginyl; carbobenzoxy-Prolyl-Arginyl; Boc-d-Phenylalanyl-Prolyl-Arginyl; d-Phenylalanyl-Prolyl-Arginyl; α-carbobenzoxy-ε-Boc-Lysyl; ε-Boc-Lysyl; Boc-d-Valyl-Leucyl-ε-Boc-Lysyl; d-Valyl-Leucyl-Lysyl; Leucyl-Arginyl; Boc-d-Valyl-Leucyl-Arginyl; d-Valyl-Leucyl-Arginyl; Lysyl(ε-carbobenzoxy)-Arginyl; Lysyl(ε-carbobenzoxy)-Lysyl(ε-carbobenzoxy)-Arginyl; and d-Valyl-Lysyl(ε-carbobenzoxy)-Lysyl(ε-carbobenzoxy)-Arginyl.

6. The synthetic substrate of claim 1, wherein R is carbobenzoxy-Arginyl.

7. The synthetic substrate of claim 1, wherein R is Arginyl.

8. The synthetic substrate of claim 1, wherein R is carbobenzoxy-Proyl-Arginyl.

9. The synthetic substrate of claim 1, wherein R is Boc-d-Phenylalanyl-Prolyl-Arginyl.

10. The synthetic substrate of claim 1, wherein R is d-Phenylalanyl-Prolyl-Arginyl.

11. The synthetic substrate of claim 1, wherein R is α-carbobenzoxy-ε-Boc-Lysyl.

12. The synthetic substrate of claim 1, wherein R is ε-Boc-Lysyl.

13. The synthetic substrate of claim 1, wherein R is Boc-d-Valyl-Leucyl-Lysyl.

14. The synthetic substrate of claim 1, wherein R is d-Valyl-Leucyl-Lysyl.

15. The synthetic substrate of claim 1, wherein R is Leucyl-Arginyl.

16. The synthetic substrate of claim 1, wherein R is Boc-d-Valyl-Leucyl-Arginyl.

17. The synthetic substrate of claim 1, wherein R is d-Valyl-Leucyl-Arginyl.

18. The synthetic substrate of claim 1, wherein R is Lysyl(ε-carbobenzoxy)-Arginyl.

19. The synthetic substrate of claim 1, wherein R is Lysyl(ε-carbobenzoxy)-Lysyl(ε-carbobenzoxy)-Arginyl.

20. The synthetic substrate of claim 1, wherein R is d-Valyl-Lysyl-(ε-carbobenzoxy)-Lysyl(ε-carbobenzoxy)-Arginyl.

* * * * *